United States Patent [19]
Burstein et al.

[11] Patent Number: 5,897,991
[45] Date of Patent: *Apr. 27, 1999

[54] HIGHLY SENSITIVE IMMUNOCYTOCHEMICAL METHOD FOR DIAGNOSIS OF MALIGNANT EFFUSIONS

[75] Inventors: David E. Burstein; Richard S. Haber, both of New York, N.Y.

[73] Assignee: The Mount Sinai Medical Center, New York, N.Y.

[ * ] Notice: This patent is subject to a terminal disclaimer.

[21] Appl. No.: 08/984,954

[22] Filed: Dec. 4, 1997

Related U.S. Application Data

[63] Continuation-in-part of application No. PCT/US96/09503, Jun. 7, 1996, which is a continuation-in-part of application No. 08/473,434, Jun. 7, 1995, Pat. No. 5,698,410.

[51] Int. Cl.$^6$ ........................ G01N 33/574; G01N 33/53; C12Q 1/68
[52] U.S. Cl. .............................. 435/6; 435/7.2; 435/7.23; 436/63; 436/64
[58] Field of Search ..................................... 435/7.2, 7.23, 435/6; 436/63, 64, 813

[56] References Cited

U.S. PATENT DOCUMENTS 5,698,410  12/1997  Burstein et al. ........................ 435/7.23

OTHER PUBLICATIONS

Y. Noguchi, et al., "Expression of Glucose Transporters and Insulin Resistance in Human GI Cancer," *Proceedings of the American Association for Cancer Research*, 36:205 (Mar. 1995).

M. Younes, et al., "Most Non–Small Cell Lung Cancers (LCA) Express the Human Erythrocyte Glucose," *Proceedings of the American Association for Cancer Research*, 36:249 (Mar. 1995).

G. Boden, et al., "Glucose Transporter Proteins in Human Insulinoma," *Annals. of Internal Medicine*, 121 (2) :109–112 (Jul. 1994).

R. S. Brown, and R. L. Wahl, "Overexpression of Glut–1 Glucose Transporter in Human Breast Cancer," *Cancer*, 72 (10) :2979–2985 (Nov. 1993).

P. Mellanen, et al., "Expression of Glucose Transporters in Head–and–Neck Tumors," *Int. J. Cancer*, 56:622–629 (1994).

Y. Nagase, et al., "Immunohistochemical Localization of Glucose Transporters in Human Renal Cell Carcinoma," *The Journal of Urology*, 153:798–801 (Mar. 1995).

T. Yamamoto, et al., "Over–Expression of Facilitative Glucose Transporter Genes in Human Cancer," *Biochemical and Biophysical Research Communications*, 170 (1) :223–230 (1990).

R. S. Brown, et al., "Intratumoral Distribution of Tritiated–FDG in Breast Carcinoma: Correlation between Glut–1 Expression and FDG Uptake," *The Journal of Nuclear Medicine*, 37(6) :1042–1047 (Jun. 1996).

D. Kornrumpf, et al., "Overexpression of Glut–1 Glucose Transporter in Human Pancreatic Cancer—An Immunohistochemical Study," *The Journal of Nuclear Medicine*, 36(5) :211P Proceedings of the 42 Annual Meeting (May 1995), Abstract.

S. Nagamatsu, et al., "Expression of Facilitative Glucose Transporter Isoforms in Human Brain Tumors," *Journal of Neurochemistry*, 61 (6) :2048–2053 (Dec. 1993).

T. Higashi, et al., "Overexpression of GLUT–1 Glucose Transporter in Human Malignant Pancreatic Tumors Immunohistochemical Study of Glucose–1,2,3,4 and 5 Glucose Transporters," *Gastroenterology*, 110 (4) :A528 (Apr. 1996), Abstract.

M. Younes, et al., "Glucose Transporter Glut 1 is Frequently Expressed in Colon Cancer," U.S. Canadian Acad. Pathology 1995 Meeting, Mar. 11–19, p. 71A, Abstract No. 404 (1995).

S. Baer et al., Expression of Glut1 and Glut3 in Squamous Cell Carcinomas of the Head and Neck (SCCNHN), Laboratory Investifation 76:113A (1997) Annual Meeting Abstracts, Abstract.

M. Younes, et al., "Glut1 and Glut3 Are Significant Prognostic Indicators in State I Non–Small Cell Lung Carcinoma," Laboratory Investigation 74:165A (1996) Annual Meeting Abstracts, Abstract.

Juarez et al., "Glut1 Expression in Transitional Cell Carcinoma of the Urinary Bladder Correlates with Agressive Biologic Behavior," Laboratory Investigation 74:75A (1996), Annual Meeting Abstracts, Abstract.

*Primary Examiner*—Toni R. Scheiner
*Attorney, Agent, or Firm*—Hamilton, Brook, Smith & Reynolds, P.C.

[57] ABSTRACT

Disclosed is a method of detecting malignancy in a body cavity effusion. Also disclosed is a method of distinguishing a benign hyperplastic lymph node from a lymph node involved by a low grade follicular lymphoma. Also disclosed is a method of distinguishing a benign tumor from a malignant tumor which overexpresses GLUT-1.

15 Claims, No Drawings

HIGHLY SENSITIVE IMMUNOCYTOCHEMICAL METHOD FOR DIAGNOSIS OF MALIGNANT EFFUSIONS

RELATED APPLICATIONS

This application is a Continuation-in-Part of International Application PCT/US96/09503, filed on Jun. 7, 1996, which is a continuation-in-part of U.S. patent application Ser. No. 08/473,434 filed on Jun. 7, 1995, now U.S. Pat. No. 5,698, 410, the entire teachings of which are hereby incorporated into this application by reference.

BACKGROUND OF THE INVENTION

Abnormal collections of fluids in a body cavity of an individual, referred to as effusions, are often caused by malignant tumors. An effusion can also be the first sign that a tumor which had been surgically removed or had undergone remission is metastasizing. However, an effusion can have many causes that are unrelated to cancer, e.g. heart failure, liver dysfunction and pneumonia. Presently, the standard method of determining whether an effusion is caused by a cancer from an effusion resulting from other causes is to remove some of the effusion fluid, isolate the cells contained therein, and examine the cells morphologically. However, this method of diagnosis leaves a significant percentage of cancers undetected. A more reliable method of determining whether an effusion is cancer-related would allow earlier intervention with treatment and can increase the likelihood of better clinical outcomes.

In many cases it is difficult to determine whether a tumor or nodule is malignant without surgically removing the suspected tissue. For example, when a thyroid nodule is detected, one method for distinguishing benign from malignant nodules is cytologic examination of cells obtained by fine needle aspiration (FNA). Routine cytologic examination of FNA specimens is, however, far from satisfactory. Even when adequate specimens are obtained the cytologic report is often indeterminate because of the inherent inability of routine cytology to distinguish benign from malignant follicular neoplasms (adenoma vs. carcinoma) when a microfollicular pattern is seen. This frequently leads to surgical excision of these nodules, the majority of which are ultimately found to be benign (Mazzaferri, E. L., *New Engl. J. Med.* 328:553–559, 1993). In addition, concern about false-negative reports when the cytologic diagnosis is benign may also lead to surgery. As a result, the majority of patients who have thyroid surgery for nodules turn out to have benign disease, even with the extensive use of FNA and routine cytology (Mazzaferri, E. L., *Am. J. Med.* 93:359–362, 1992; Cusick, et al., *Br. Med. J.* 301:318–321, 1990). Consequently, there is a need for a more accurate method of distinguishing between malignant and benign tumors prior to surgery.

SUMMARY OF THE INVENTION

The present invention is based on the discovery that cancer (malignant) cells in body cavity effusions can be detected and distinguished from noncancer cells by immunostaining of the transmembrane glucose transporter protein GLUT-1 in malignant effusions. As discussed herein, GLUT-1 is overexpressed in many malignancies. Sites of origin of GLUT-1 positive malignant cells in effusions included ovary, lung, breast, biliary tract, endometrium, and carcinomas of unknown primary.

The degree of GLUT-1 overexpression can also be used as a prognostic indicator. It has been found that the degree of GLUT-1 overexpression in cancerous tumor cells correlates with the degree of aggressiveness of the tumor. Thus, the degree of GLUT-1 overexpression can be used as an aid in determining the prognosis of individuals with a cancerous tumor which overexpresses GLUT-1. For example, colon cancer patients were found to be about 2.4 times more likely to die from the disease when more than about 50% of the cells in a tissue sample obtained from their tumors stained positive for GLUT-1 than when less than about 50% of the cells stained positive for GLUT-1 (Example 3).

It has also been found unexpectedly that GLUT-1 is underexpressed in neoplastic follicles from low grade follicular lymphomas compared with benign hyperplastic lymph nodes. Consequently, these lymphatic malignancies can be identified by diminished or absent GLUT-1 immunostaining of follicles.

Another aspect of the present invention is a method of distinguishing between malignant and benign tumors based on assessment of expression of transmembrane GLUT-1 in cells from tissue samples. That is, overexpression of transmembrane GLUT-1 has been shown to aid in distinguishing between malignant and benign tumors; overexpression can be identified by immunostaining or by quantitating the amount of GLUT-1 mRNA produced by the tumor cells. It is also possible that GLUT-1 DNA can also be assessed, for example by identifying multiple copies of the gene or mutations in the control region. Cancers which overexpress GLUT-1 include ovary, lung, breast, biliary tract, endometrium, squamous cell carcinoma of head and neck origin, leiomyosarcoma, kidney, thyroid, bladder, colon and carcinomas of unknown primary.

The present invention is a method of assessing malignancy in a sample of cells or cellular material, e.g. a tissue sample or effusion, taken from an individual to be assessed for the presence of malignancy. The degree of GLUT-1 expression in the sample is assessed and compared with the degree of GLUT-1 expression in an appropriate standard or control having a known GLUT-1 expression characteristic.

In one embodiment, the present invention is a method of detecting malignancy in a body cavity effusion. A cytologic preparation, e.g., a cell block, smear or centrifuge specimen, is prepared from a body cavity effusion, thereby producing a test preparation. The level of GLUT-1 expression (i.e., in the test preparation) is then assessed. The level of GLUT-1 expression in an appropriate control is compared with the level of GLUT-1 expression in cells in the test preparation. The control is a cytological preparation produced from a benign body cavity effusion; GLUT-1 expression in cells in the control is assessed and is the level of GLUT-1 expression to which the GLUT-1 level in the test preparation is compared (the effusion being assessed). A lower level of GLUT-1 expression in the control compared with the level of GLUT-1 expression in cells from the effusion being assessed is indicative of malignancy in the body cavity effusion being assessed. Because cells in benign effusions typically express little or no GLUT-1, positive GLUT-1 expression in the test preparation, as indicated, for example, by positive immunostaining for GLUT-1, is indicative of malignancy in the effusion. Established laboratory or clinical methods can be used to confirm assessment of cells as malignant or benign.

Another embodiment of the present invention is a method of distinguishing a benign hyperplastic lymph node from a lymph node involved by a low grade follicular lymphoma. In this embodiment, a tissue sample is obtained from a section of a lymph node suspected of being involved by a low grade follicular lymphoma. The level of GLUT-1 expression in the cells from the tissue sample is assessed. The level of GLUT-1 expression in an appropriate control is compared with the level of GLUT-1 expression in the cells of the tissue sample being assessed. The control is the level of GLUT-1 expressed in cells from a benign hyperplastic lymph node. A lower level of GLUT-1 expression in the tissue sample being assessed, compared with the level in the control, indicates that the tissue sample being assessed is involved by a low grade follicular lymphoma. Because cells in follicular lymphomas typically express little or no GLUT-1, the absence of GLUT-1 expression in follicles in the test preparation, as indicated, for example, by the absence of immunostaining for GLUT-1, is indicative of a low grade follicular lymphoma. Established laboratory or clinical methods can be used to confirm the assessment that cells are malignant or benign.

Yet another embodiment of the present invention is a method of distinguishing a benign tumor from a malignant tumor which overexpresses GLUT-1. A tissue sample is obtained from a section of a tumor suspected of being malignant. GLUT-1 expression in cells from the tissue sample is assessed. The level of GLUT-1 expression in an appropriate control is compared with the level of GLUT-1 expression in the tissue sample being assessed. The control is the amount of GLUT-1 expressed in the cells from a tissue sample obtained from a section of a non-malignant tissue from the same tissue type as the tissue sample being assessed. A higher level of GLUT-1 expression in the sample being assessed compared with the control indicates that the tissue sample being assessed is involved by a malignant tumor. Because cells in benign tissue samples typically express little or no GLUT-1, positive GLUT-1 expression in the test preparation, as indicated, for example, by positive immunostaining for GLUT-1, indicative of a malignant tumor. Established laboratory or clinical methods can be used to confirm the assessment that cells are malignant or benign.

Yet another embodiment of the present invention is a method of aiding in determining a prognosis for an individual with a cancerous tumor which overexpresses GLUT-1, e.g. determining the aggressiveness of the tumor. The method comprises determining the degree of GLUT-1 expression in cells from a tissue sample obtained from the cancerous tumor and correlating the degree of GLUT-1 expression in cells from the tissue sample with the clinical outcome of the individual. The clinical outcome is assessed by determining if the degree of GLUT-1 expression is above or below a threshold or thresholds which have been predetermined to define different prognostic subgroups. A level of GLUT-1 expression which is above the threshold is indicative of a poorer prognosis than if the level of GLUT-1 expression is below the threshold.

Since immunocytochemistry is relatively inexpensive and routinely used in clinical pathology laboratories, GLUT-1 immunostaining has the potential for widespread clinical application.

DETAILED DESCRIPTION OF THE INVENTION

Many types of cancer cells have markedly increased glucose utilization, resulting from a predominantly glycolytic rather than oxidative utilization of glucose, even in the presence of oxygen (Warburg, O., *Science* 123:309–314, 1956). Because the metabolism of glucose to lactate yields only 2 moles of ATP/mole glucose, as opposed to 36 moles of ATP produced by oxidative metabolism, cancer cells are forced to increase their glucose utilization many-fold compared to normal cells. Since glucose transport across the plasma membrane is rate-limiting for glucose utilization in cancer cells and many normal cells as well, cancer cells have markedly increased glucose transport rates (Hatanaka, M., *Biochem. Biohys. Acta.* 355:77–104, 1974; Weber, M. et al., *J. Cell Physiol.* 89:711–721, 1976; Elbrink, J. and I. Bihler, *Science* 188:1177–1184, 1975). Indeed, transformation of cultured cells is accompanied by a five- to ten-fold increase in glucose transport and in glucose transporter gene expression (Flier, J. S. et al., *Science* 235:1492–1495, 1987; Birnbaum, M. J. et al., *Science* 235:1495–1498, 1987).

The facilitated diffusion of glucose into cells is mediated by a family of five homologous proteins, GLUT-1-GLUT-5, which were cloned and identified from 1986–1989 (Pessin, J. E. and G. L. Bell, *Annu. Rev. Physiol.* 54:911–930, 1992). The glucose transporter isoforms differ in their tissue distribution and functional characteristics. The GLUT-1 isoform is the focus of the present application.

Although GLUT-1 is expressed in many organs, immunohistochemical studies demonstrate its expression mainly in erythrocytes (red blood cells) and in cells which constitute blood-tissue barriers. For example, in brain GLUT-1 is seen only in the capillary endothelium of the blood-brain barrier (Boado, R. J. and Wm. Pardridge, *Biochem. Biophys. Res. Commun.* 166:175, (1990)); in muscle it is found only in the perineurium of innervating nerves (blood-nerve barrier) (Froehner, S. C. et al., *J. Neurocytol.* 17:173–178, 1988)). In addition, in routinely prepared tissue sections of skin and squamous epithelia, GLUT-1 is found in basal cells by immunostaining. However, benign parenchymal cells of most tissues do not stain for GLUT-1 immunohistochemically, even with the sensitive avidin-biotin-peroxidase method.

Experimental evidence indicates that malignant cells overexpress GLUT-1. Transformation of cultured cells with src and ras oncogenes or sarcoma virus promptly increases glucose transporter protein and GLUT-1 mRNA by 5–10 fold (Flier, J. S. et al., *Science* 235:1492–1495, 1987; Birnbaum, M. J. et al., *Science* 235:1495–1498, 1987). GLUT-1 mRNA in a variety of gastrointestinal cancers (Yamamoto, T. et al., *Biochem. Biophys. Res. Commun.* 170:223–230, 1990) and in hepatoma (Su, T-S. et al., *Hepatology* 11:118–122, 1990) is expressed at higher levels than in corresponding normal tissue. High levels of GLUT-1 mRNA (Northern blotting) and protein (immunohistochemistry) were also found in a series of head-and-neck squamous cell carcinomas (Mellanen, P. et al., *Int. J. Cancer* 56:622–629, 1994). An immunohistochemical study of GLUT-1 expression in breast cancer (using archival formalin-fixed paraffin sections) also found variably increased staining, whereas normal breast tissue stained only weakly or not at all (Brown R. S. and R. L. Wahl, *Cancer* 72:2979–85, 1993). The only other isoform which has been thought to be overexpressed in cancer is GLUT-3, based on reports of increased GLUT-3 mRNA without measurement of GLUT-3 protein (Yamamoto, T. et al., *Biochem. Biophys. Res. Commun.*, 170:223–230, 1990; Mellanen, P. et al., *Int. J. Cancer* 56:622–629, 1994). However, Northern blotting for GLUT-3 mRNA has proved to be a false indicator of the presence of GLUT-3 protein in many tissues (Haber, R. S. et al., *Endocrinology* 132:2538–2543, 1993), and we have not detected GLUT-3 protein in immunoblots from a wide variety of human cancers.

The present invention is a method of diagnosing cancers. A "method of diagnosing cancer" can be used to distinguish between malignant and benign tissue, for example determining whether a tumor or nodule is benign or malignant. It can also be used to determine the presence or absence of cancer in an individual. For example, an effusion, which can have many other causes, is often the first sign that a cancer exists or that a tumor which had been surgically removed or gone into remission, has metastasized or recurred. The methods of the present invention can determine whether an effusion is due to a cancer whose primary site may be known or unknown or is due to other causes. Alternatively, the methods of the present invention can be used as an aid in diagnosing cancer. An "aid in diagnosing cancer" is used in conjunction with other medical tests to determine the presence or absence of cancer in an individual or determine whether particular tissue is malignant or benign.

An effusion is an abnormal collection of fluid in a body cavity. The present method is applicable to effusions from body cavities, such as the abdominal cavity (the peritoneal cavity), the pleural cavities (the spaces that line lung) and the pericardial cavity (the space that lines the heart). Methods of obtaining an effusion are well known in the art and typically involve puncturing the chest wall or abdominal wall with a needle and evacuating the fluid.

A cytological preparation is a preparation of biological material from an effusion. Typically, a cytological cell block is obtained by providing a sample of an effusion and concentrating the cells contained therein. Cells are concentrated from an effusion by, for example, centrifugation. After concentration, the cells are typically fixed in formalin or alcohol and imbedded in paraffin as is routinely done for tissue in surgical pathology.

As used herein, a "tissue sample" is a collection of cells taken from tissue and is used to obtain a determination of GLUT-1 expression that is sufficiently precise to distinguish malignant cells which overexpress GLUT-1 from non-malignant cells. Methods of obtaining tissue samples are well known in the art and include obtaining samples from surgically excised tissue. Tissue samples and cellular samples can also be obtained without the need for invasive surgery, for example by puncturing the chest wall or the abdominal wall or from masses of breast, thyroid or other sites with a fine needle and withdrawing cellular material (fine needle aspiration biopsy). The tissue samples can then be fixed in formalin or alcohol and imbedded in paraffin as is routinely done for surgical pathology. Alternatively, the cells can be applied directly from the fine needle to a microscope slide.

An appropriate control is the level of GLUT-1 expression in cells taken from a benign body cavity effusion or a sample taken from benign tissue of the same type that is being assessed. The level of GLUT-1 expression can be determined prior to, simultaneously with, or subsequent to the determination of the level of GLUT-1 expression in the tissue or effusion being assessed and is determined by the same technique as in the tissue sample or effusion being assessed, for example by immunostaining. Benign effusions and benign tumors show non-existent staining to weak staining of cells; malignant effusions and tumors show intense staining of the membranes of malignant cells. Benign follicles show positive staining whereas malignant follicles from low-grade lymphomas are nonstaining for GLUT-1. Staining properties of benign and malignant cells differ so dramatically and thus, are readily distinguishable from one another. Therefore, in many cases a positive or negative control is not needed because the staining properties of malignant cells are so distinctive. Thus, positive staining in a cytological preparation or tissue sample is generally indicative of malignancy in the effusion or tumor from which the cytological preparation or tissue sample, respectively, were obtained, without the need for comparing the degree of immunostaining to a control. Similarly, the absence of staining in follicles of a tissue sample obtained from lymph node is generally indicative of a low grade follicular lymphoma in the lymph node without the need for comparing the degree of immunostaining to a control.

The levels of GLUT-1 expression from tissue samples or cytological preparation can be determined by immunostaining. The primary antibody can be, for example, a well-characterized rabbit antiserum raised against a 13-amino acid peptide corresponding to the C-terminal of GLUT-1 (Hasper, H. C. et al., *J. Biol. Chem.* 263:398–403, 1988), obtained commercially (East Acres Biologicals). This antibody recognizes both rat and human GLUT-1 which share the peptide sequence, but does not crossreact with other GLUT isoforms, which are highly divergent at the C-terminus. Analogously obtained polyclonal or monoclonal antibodies can also be used. Bound antibody is detected by a routine avidin-biotin-peroxidase method (for example, Vectastain kit, VECTOR) or equivalent immunostaining methods. To demonstrate the specificity of staining, antiserum pre-incubated with the immunizing peptide (20 $\mu$g/ml) is used to stain parallel tissue sections.

As described in the examples, the antiserum gave strong specific (peptide-compatible) staining of GLUT-1 in capillary endothelium in brain (blood-brain barrier), in erythrocytes, in basal cells of benign squamous epithelia, and in perineurium of peripheral nerve, all of which are sites of high GLUT-1 expression. In contrast, parenchymal cells of a wide variety of normal tissues were negative for GLUT-1. Antibody dilution can be any dilution which is useful to produce sufficient staining to enable one to distinguish malignant cells from benign cells. Antibody dilution can be, for example, 1:100 to 1:2000, and in a particular embodiment 1:500 to 1:200. In one embodiment, an antibody dilution of 1:500 was found to be optimal.

GLUT-1 expression in cell blocks prepared for routine cytology from benign and malignant pleural and peritoneal effusions has also been studied. Immunostaining methodologies were applied to the detection of GLUT-1 in cytologic preparations of body cavity effusions. Using standard avidin-biotin immunostaining, cell blocks were examined from 76 body cavity effusions or washings. Of 58 technically appropriate cell block preparations, GLUT-1 staining occurred in 30 out of 32 malignant effusions. Sites of origin included ovary, lung, breast, biliary tract, endometrium, and carcinomas of unknown primary. only the mesothelioma tested stained positively for GLUT-1. Characteristic staining pattern consisted of dense, linear staining of the plasma membrane, with accentuation at cell-cell borders, with or without cytoplasmic staining. Specificity of GLUT-1 staining was further defined by preincubation of antiserum with the immunizing 13 amino acid peptide from the carboxyl terminal of GLUT-1. Red blood cells showed similar membrane staining, consistent with previous reports. Of 26 benign effusions, 21 were nonstaining, and 5 showed rare mesothelial cells with equivocal to very weak membrane staining which was readily distinguishable from the characteristic strong staining of malignant cells and easily distinguished by benign morphological characteristics; at least 3 of these 5 cases were from patients with cirrhosis. In all other cases, mesothelial cells, histiocytes and other inflammatory cells were nonstaining.

These findings show that GLUT-1 immunostaining alone or in a panel of markers, for example immunohistochemical or histochemical markers, can be used in diagnostic cytopathology.

Other suitable methods can be used to determine expression of GLUT-1. For example, GLUT-1 expression can be determined by identifying the presence of GLUT-1 mRNA or by assessing the quantity of GLUT-1 mRNA in cells from a tissue sample or from an effusion. The presence or amount of mRNA in the cells of the tissue sample or effusion can be assessed by methods known in the art, for example, by reverse transcribing the mRNA present in the cells to obtain cDNA which includes GLUT-1 cDNA, i.e., cDNA hybridizable to GLUT-1 mRNA. The presence of GLUT-1 cDNA is indicative of the presence of GLUT-1 mRNA in the cells from the tissue sample or effusion; the level of GLUT-1 cDNA corresponds to the amount of GLUT-1 mRNA in the cells taken from the tissue sample or effusion. The presence of GLUT-1 cDNA can be determined by polymerase chain reaction (PCR). The level of GLUT-1 cDNA can be assessed by quantitative PCR methods, as disclosed, for example, in Alard et al., *Biotechniques*, 15:730 (1993), the entire teachings of which are incorporated herein by reference. "Quantitative PCR" refers to methods which are able to quantitate the amount of cDNA derived from reverse transcription of mRNA in cells from a tissue sample or effusion.

The mRNA in the cells obtained from a tissue sample can be reverse transcribed by methods known in the art which are disclosed, for example, in Chapter 8 of "Molecular Cloning: A Laboratory Manual", second edition, by J. Sambrook, E. F. Fritsch and T. Maniatis, Cold Spring Harbor Press, 1989, the entire teachings of which are incorporated herein by reference.

The detection of GLUT-1 cDNA by PCR can be carried out with primers suitable for amplifying the GLUT-1 cDNA by methods known in the art and described, for example, in Chapter 14 of "Molecular Cloning: A Laboratory Manual", second edition, by J. Sambrook, E. F. Fritsch and T. Maniatis, Cold Spring Harbor Press, 1989, the entire teachings of which are incorporated herein by reference. The presence of amplified cDNA can be, for example, detected electrophoretically.

Quantitative PCR is carried out, for example, by amplifying, as described above, according to standard PCR methods using a primer which is modified to allow capture of the resulting product onto a solid surface. For example, the 5' or 3' primer can be biotinylated at the 5' terminus or 3' terminus, respectively, to allow capture of the resulting product onto avidin-coated microplates.

The product attached to the solid surface is then quantitated, for example, by hybridizing to an oligonucleotide probe having a quantifiable label attached thereto. A "quantifiable label" can be, for example, a radioactive atom or group. The level of GLUT-1 expression is then assessed by determining the level of radioactivity in the sample. Alternatively, a "quantifiable label" is a group or moiety such as digoxigenin. The PCR product is quantitated by addition of 1) an anti-digoxigenin antibody that is coupled with alkaline phosphatase and 2) a colorigenic substrate for alkaline phosphatase, followed by absorptometry. Optionally, the result can be normalized with respect to a cDNA standard curve.

Other PCR based methods of assessing the level of GLUT-1 mRNA present in a sample are known in the art and are encompassed within the present invention. One example is disclosed in Wang et al., *Proc. Nat. Acad. Sci. USA* 86:9717 (1989), the entire teachings of which are hereby incorporated by reference.

In addition to being useful to distinguish benign from malignant thyroid disease, GLUT-1 immunostaining is useful as a prognostic indicator in individuals with colon carcinomas.

The degree of GLUT-1 immunostaining and its correlation to the clinical aggressiveness of other tumors which overexpress GLUT-1, e.g., breast, biliary tract, pancreas, skin, ovaries, endometrium, cervix, biliary tract, pancreas, skin, bladder, lung, head and neck carcinomas and others is the basis for applying the method described herein to a wide variety of tumor types.

An "aid in determining a prognosis" refers to a test or assay which can be used to determine the prognosis of an individual with a cancerous tumor which overexpresses GLUT-1. An "aid in determining a prognosis" can be used alone or in combination with other tests or assays. As used herein, a "prognosis" is a determination of the life expectancy of an individual with a cancerous tumor in which the tumor cells overexpress GLUT-1. Alternatively, a "prognosis" is a determination of the likelihood that the individual will die from the tumor or will respond to treatments for the tumor, e.g. that the treatments will result in stabilization or shrinkage of the tumor or that the treatments will result in the tumor growing or metastasizing slower than in the absence of the treatments. Thus, an aid in determining a prognosis can used to identify which individuals with a cancerous tumor are likely to respond to aggressive treatments.

The "clinical aggressiveness" of a cancerous tumor refers to, for example, how quickly the tumor is growing, how quickly the tumor is metastasizing or how quickly the tumor will result in the patient succumbing to the disease. The "clinical aggressiveness" of a cancerous tumor can also refer to the likelihood that the tumor will respond to treatment, as discussed above.

The "degree" of GLUT-1 overexpression refers to the extent to which GLUT-1 is overexpressed in the tissue sample taken from a tumor which expresses GLUT-1 compared with normal tissue of the same type. The amount of GLUT-1 expressed in a tissue sample can be determined by any suitable method, for example by determining the amount of GLUT-1 mRNA in the tissue sample, or, preferably by immunostaining, as discussed above. Normally in most tissues, GLUT-1 is expressed either minimally or not at all. Thus, GLUT-1 overexpression in a tissue sample is typically assessed by determining the percentage of cells staining positively for GLUT-1 expression or by quantitating the overall intensity of the staining in the tissue sample. In tissue types which normally express GLUT-1, GLUT-1 overexpression can be assessed by determining the percentage of cells which stain more intensely than normal cells of the same tissue type or by comparing the intensity of staining to a suitable control, for example the overall intensity of staining of a tissue sample obtained from benign tissue of the same type as is being assessed. The degree to which the staining of the tissue sample is more intense than the control is indicative of the degree of GLUT-1 overexpression.

In one embodiment, the prognosis of an individual with a cancerous tumor which overexpresses GLUT-1 is determined by correlating the degree of GLUT-1 overexpression with the clinical outcome of the individual or by correlating the degree of GLUT-1 expression with predefined standards which are predictive of the individual's clinical outcome. The degree of GLUT-1 overexpression is correlated with the clinical outcome of the individual by assessing the degree of GLUT-1 overexpression, for example by calculating the percentage of tumor cells showing positive GLUT-1 staining, and determining whether the degree of overexpression is above or below a threshold or thresholds. The threshold or thresholds have been pre-determined to define different prognostic subgroups by taking a statistically significant cohort of patients with the same kind of cancer as the test patient for whom clinical outcomes are known, and thereby establishing thresholds above or below which different prognostic subgroups have been identified. The prognostic subgroup to which an individual belongs determines the individual's prognosis, for example, the probability or likelihood that the individual being tested will die from the cancer or will survive a given length of time. For example, it has now been found that an individual with colon cancer has about a 2.4 times greater probability of dying from the cancer if more than about 50% of the cells in a tissue sample taken from the colon tumor immunostain positively for GLUT-1 than if less than about 50% of the cells immunostain positively for GLUT-1.

A prognosis can also be the likelihood or probability that an individual with a cancerous tumor which overexpresses GLUT-1 will respond to a particular treatment. The degree of GLUT-1 expression is determined in a statistically significant cohort of patients with the same kind of cancer as the test patient, for whom the responses to the particular type of treatment is known. From these data a threshold or thresholds for GLUT-1 expression can be established which define different prognostic subgroups. The prognostic subgroup to which an individual belongs is determined by the level of GLUT-1 expression in the individual's tumor. Individuals belonging to the same prognostic subgroup are likely to have similar responses to a particular treatment.

An individual "responds to a treatment", for example, when the individual's life is extended as a result of the treatment, compared with individuals who have not undergone the treatment. Alternatively, an individual "responds to a treatment" when the individual's symptoms are ameliorated as a result of the treatment compared with individuals who have not undergone the treatment.

As discussed above, many cancers overexpress GLUT-1. Quite unexpectedly, it has been found that GLUT-1 is underexpressed in neoplastic follicles from low grade follicular lymphomas. Tissue samples taken from lymph nodes showing neoplastic lymph follicles were observed to exhibit less immunostaining than normal follicle-like "germinal centers". This observation can be used as the basis for a method of diagnosing and as an aid in diagnosing low grade follicular lymphomas. These tumors can be distinguished from normal tissue by assessing GLUT-1 expression in the follicles of the lymph node. Less GLUT-1 expression in the tissue sample than in an appropriate control, e.g. the level of expression typically observed in non-malignant lymphoid follicles, or the absence of GLUT-1 expression in follicles is indicative of a low grade follicular lymphoma. GLUT-1 expression can be determined, for example, by immunostaining, as described above. Low grade follicular lymphomas show less follicular staining than normal follicles in lymph node biopsies. Typically, GLUT-1 low grade follicular lymphomas can be identified by the absence of immunostaining.

The invention is illustrated by the following examples, which are not to be construed as limiting in any way.

EXAMPLE 1

Distinguishing Malignant Thyroid Nodules From Benign Thyroid Nodules Using Immunocytochemical Staining for GLUT-1 Glucose Transporter Preparation of cytologic "touch prep" slides and frozen histologic sections from thyroid tissue. Glass slides were coated with aminoalkylsilane to promote cell adhesion. The slides were dabbed against a cut surface of a freshly-excised tumor, and immediately sprayed with ethanolic cytology fixative. Routine frozen sections were fixed in ethanol.

Fine needle aspirates of thyroid tissue. Freshly-excised surgical thyroid tissue were subjected to fine needle aspiration using a 22-gauge needle, 10-cc syringe, and Cameco syringe pistol. Aspirates were smeared between two glass slides and immediately sprayed with cytology fixative as for routine clinical FNA. This procedure is meant to mimic standard clinical FNA as closely as possible.

GLUT-1 immunostaining. GLUT-1 protein in cytologic preparations was detected by standard avidin-biotin-peroxidase immunocytochemistry. Paraffin-imbedded tissue specimens on glass slides are rehydrated through graded ethanol, washed in phosphate-buffered saline (PBS), and blocked with 5% goat serum in PBS. They were then incubated with rabbit anti-GLUT-1 serum at 1:500 dilution (with or without pre-incubation of the antiserum with the immunizing peptide at 20 $\mu$g/ml to confirm signal specificity). Both GLUT-1 antiserum and GLUT-1 peptide are commercially available from East Acres Biologicals (Southbridge, Mass.). The slides were then washed and incubated with secondary antibody (biotinylated goat and anti-rabbit 1:200). After blocking of endogenous peroxidase with 0.3% $H_2O_2$, bound antibody was detected with avidin-biotin-peroxidase complex (Vectastain kit, Vector Labs) using diaminobenzidene as a chromogen. The slides were counter-stained with hematoxylin, dehydrated in graded ethanol and xylene, and mounted with coverslips.

Microscopic interpretation. Immunostained specimens were graded for specific GLUT-1 staining without prior knowledge regarding the source of the specimen. The criteria for specific staining were inhibition of the signal by competition with the immunizing GLUT-1 peptide. Cellular GLUT-1 is known to be distributed between the plasma membrane and intracellular vesicles (Yang, J. et al., *J. Biol. Chem.* 267:10393–10399, 1992). The subcellular pattern of staining (peripheral vs. intracellular) and the intensity of staining (1+ to 4+) was also noted.

For correlation of GLUT-1 immunostaining results with routine cytologic diagnosis in thyroid, parallel slides were stained (Papanicolaou) and examined microscopically by the same blinded observer. Aspirates were assigned cytologic diagnosis of: a) benign, b) malignant or suspicious for malignancy, c) indeterminate, or d) inadequate specimen.

To confirm specificity parallel tissue sections were stained using antiserum that had been pre-incubated with the immunizing peptide. There were 31 benign cases (19 follicular adenoma, 1 Hurthle cell adenoma, 6 nodular goiter, 3 lymphocytic thyroiditis, 2 Graves' disease) and 23 cases of thyroid cancer (9 papillary, 4 follicular variant of papillary, 5 follicular, 1 Hurthle cell, 2 anaplastic, 2 medullary). Normal thyroid tissue adjacent to nodules showed no thyrocyte staining in any case. As expected, there was strong specific GLUT-1 staining in erythrocyte membranes and in perineurium. No GLUT-1 staining was seen in thyrocytes in benign nodular tissue, except for a single case of thyroiditis in which some foci of Hurthle cells showed weak staining. Among the thyroid cancers, 9/23 (39%) showed GLUT-1 staining in tumor cells. This included 6/13 cases of papillary carcinoma and its follicular variant, 1/5 cases of follicular carcinoma and 2/2 cases of anaplastic carcinoma. Tumor cell GLUT-1 staining was seen in two patterns: focal circumferential plasma membrane staining at the center of tumor cell nests, or asymmetric staining of the basilar aspect of tumor cells adjacent to stroma in some cases of papillary carcinoma. We conclude that GLUT-1 protein is frequently overexpressed in thyroid cancer. GLUT-1 immunostaining may be potentially useful in the cytologic diagnosis of thyroid nodules.

EXAMPLE 2

GLUT-1 Is a More Sensitive and Selective Marker of Malignancy Than CEA in Body Cavity Effusions and Washes In the present study, GLUT-1 was compared to EMA, CEA and Leu-M1, three commonly used malignancy markers in effusions.

Materials and Methods.

Cell blocks from 38 malignant and 42 benign effusions or washes were immunostained with polyclonal anti-GLUT-1, and monoclonal anti-CEA, -Leu-M1 and -EMA using standard avidin-biotin methods.

GLUT-1 stained 35/38 malignant effusions (sites of origin: ovary, endometrium, breast, stomach, esophagus, gallbladder, lung (non-small cell), cervix, unknown primary); false positivity in occasional cells occurred in 6/42 cases, however these cells were recognizable as benign or reactive by morphology. GLUT-1 sensitivity was 92%, specificity 86%. EMA stained all malignant effusions but had false positivity in 45% of cases. CEA had sensitivity of 82% and specificity of 74%, both lower than GLUT-1. Leu-M1 had 100% specificity, but sensitivity was only 74%. Unlike GLUT-1 staining, the ease of interpreting LeuM1 and CEA staining was frequently compromised by staining of leukocytes. In 11% of malignant cases, GLUT-1 was positive when both CEA and Leu-M1 were negative. GLUT-1 was superior to either CEA, Leu-M1 or both in 21 malignant cases, and inferior in 7 such cases, as judged by large differences in the percentage or intensity of positively staining malignant cells.

GLUT-1 immunostaining was more sensitive and more specific than CEA staining. Leu-M1 had high specificity and low sensitivity; EMA had high sensitivity and very low specificity. The addition of GLUT-1 to this panel of tumor markers enhanced the accuracy, ease of interpretation and reliability of tumor diagnosis in effusions.

EXAMPLE 3

GLUT-1 Immunostaining For Obtaining a Prognosis For an Individual With Colon Cancer Formalin fixed archival colon cancer specimens were obtained from 112 colon cancers for whom long term clinical outcome with a mean follow-up of 7 years was known. The specimens were immunostained according to procedures described in Example 1. Most of the cancers, 90%, contained some degree of GLUT-1 immunostaining. The degree of staining was graded according to the percentage of tumor cells which stain for GLUT-1 as follows: the specimens were graded as less than 50% or greater than 50% staining. In the univariate analysis the mortality for colon cancer was greater in patients with greater than 50% staining: relative risk 2.4; p value 0.03. In a multivariate analysis including Dukes classification, the relative risk of death from colon cancer was 2.3 in the group with high GLUT-1 gluteone staining: p value=0.07. This data shows the degree of GLUT-1 immunostaining of colon cancer identifies high risk and low risk of groups of patients.

A statistically insignificant number of patients had cancers which showed no immunostaining. These patients had high mortality rates. These data suggest that individuals having colon tumors with little or no GLUT-1 immunostaining may define another prognostic subgroup whose members have high mortality rates resulting from their tumors.

EXAMPLE 4

Assessing GLUT-1 Expression Levels by quantitative PCR in Malignant and Benign Thyroid Tissue To identify a molecular marker which might distinguish benign from malignant thyroid modules in fine needle aspiration specimens, a sensitive and convenient quantitative PCR method was applied to measure GLUT1 mRNA expression in surgical thyroid tissue. RNA was isolated from fresh frozen tissue, and cDNA synthesized with reverse transcriptase (RT) was subjected to PCR for GLUT1 and thyroglobulin (TG) using 5'-biotinylated primers. The biotinylated PCR product was captured on avidin-coated ELISA plates and hybridized with a 3'-digoxygenin-labelled internal probe complementary to each target sequence. The PCR product was then quantitated by addition of anti-digoxygenin antibody-alkaline phosphatase and colorigenic substrate, followed by absorptometry. Signals were normalized to standard curves prepared with known amounts of plasmid containing each cDNA, and expressed as femtograms of plasmid. To correct for variations in the integrity of tissue RNA and in the efficiency of the RT reaction, GLUT1 signals were normalized to TG signals as well. Data is shown below in the Table.

TABLE

|  | Normal Thyroid n = 5 | Nodular Goiter n = 8 | Adenoma n = 17 | Papillary Carcinoma n = 8 |
| --- | --- | --- | --- | --- |
| GLUT1 | 0.48 ± 0.25 | 1.72 ± 0.82 | 2.40 ± 0.57 | 6.07 ± 1.60* |
| TG | 293 ± 142 | 1270 ± 572 | 917 ± 348 | 457 ± 107 |
| GLUT1/TG | 3.40 ± 1.18 | 9.65 ± 7.70 | 4.86 ± 1.42 | 35.9 ± 19.6** |

*$P < 0.01$ vs other groups
**$P < 0.01$ vs normal thyroid and nodular goiter, $P < 0.05$ vs adenoma.

These data demonstrate that GLUT1 and TG mRNA expression can be assessed in thyroid tissue by ELISA-PCR, and that GLUT1 expression is increased in papillary carcinoma vs benign thyroid tissue.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method of assessing malignancy in a sample of cells taken from an individual to be assessed for the presence of malignancy, wherein the degree of GLUT-1 expression in the sample is assessed and compared with the degree of GLUT-1 expression in an appropriate standard or control having a GLUT-1 expression level characteristic of benign cells, wherein a higher level of GLUT- 1 expression in the sample is indicative of malignancy.

2. The method of claim 1 wherein the method of assessing malignancy is a method of aiding in determining a prognosis for an individual with a cancerous tumor which overexpresses GLUT-1 comprising the steps of:

(a) determining the degree of GLUT-1 expression in cells from a tissue sample obtained from the cancerous tumor;

(b) correlating the degree of GLUT-1 expression in cells from the tissue sample with the clinical outcome of the individual.

3. The method of claim 2 wherein the degree of GLUT-1 expression is determined by immunostaining.

4. The method of claim 3 wherein the tumor is a colon tumor.

5. The method of claim 4 wherein the individual is 2.4 times more likely to die from the colon tumor if more than about 50% of cells in the tissue sample immunostain positive for GLUT-1 than if less than about 50% of cells in the tissue sample immunostain positive for GLUT-1.

6. The method of claim 2 wherein the tissue sample is obtained from a cancerous tumor selected from the group consisting of bladder tumors, lung tumors, head and neck tumors, cervical tumors, biliary tract tumors, pancreatic tumors, skin tumors, ovarian tumors, breast tumors and tumors of the endometrium.

7. The method of claim 1 wherein the degree of GLUT-1 expression is assessed by the steps of:
   a) reverse transcribing mRNA obtained from cells in the sample obtained from the individual to produce cDNA;
   b) subjecting the cDNA obtained in step a) to conditions suitable for amplifying a portion of of GLUT-1 cDNA, thereby producing amplified cDNA;
   c) assessing the level of amplified cDNA product obtained in step b),
      wherein the level of amplified cDNA product corresponds to the level of GLUT-1 expression in the cells of the tissue sample.

8. The method of claim 7 wherein the level of GLUT-1 cDNA in the cDNA library is determined by quantitative polyermase chain reaction.

9. A method of aiding in determining a prognosis for an individual with a cancerous tumor which overexpresses GLUT-1, comprising the steps of:
   (a) determining the degree of GLUT-1 expression in cells from a tissue sample obtained from the cancerous tumor; and
   (b) determining whether the degree of GLUT-1 expression is above or below a threshold or thresholds which have been pre-determined to define different prognostic subgroups.

10. The method of claim 9 wherein the degree of GLUT-1 expression is determined by immunostaining.

11. The method of claim 10 wherein the cancerous tumor is a colon tumor.

12. The method of claim 11 wherein the individual is 2.4 times more likely to die from the colon tumor if more than about 50% of cells in the tissue sample immunostain positive for GLUT-1 than if less than about 50% of cells in the tissue sample immunostain positive for GLUT-1.

13. The method of claim 10 wherein the tissue sample is obtained from a cancerous tumor selected from the group consisting of bladder tumors, lung tumors, head and neck tumors, cervical tumors, ovarian tumors, breast tumors and tumors of the endometrium.

14. A method of detecting malignancy in a body cavity effusion or in a tumor, comprising the steps of:

a) reverse transcribing mRNA from cells obtained from a body cavity effusion or a tissue sample from a tumor, thereby preparing cDNA;

b) subjecting the cDNA obtained in step a) to conditions suitable for amplifying a portion of GLUT-1 cDNA;

c) assessing the level of amplified cDNA obtained in step b);

d) comparing the level of amplified cDNA determined in step c) with the level of amplified cDNA obtained by the steps recited in a), b) and c) from control cells, wherein the control cells are obtained from a benign body cavity effusion or from a section of non-malignant tissue from the tissue type taken in step a),
      wherein a higher level of amplified CDNA in step c) compared with the control indicates that the effusion or tumor is involved by a malignant tumor.

15. The method of claim 14 wherein the level of GLUT-1 cDNA in the cDNA library is determined by quantitative polymerase chain reaction.

* * * * *